United States Patent
Conlan et al.

(10) Patent No.: US 6,800,184 B2
(45) Date of Patent: Oct. 5, 2004

(54) ELECTROPHORESIS SEPARATION AND TREATMENT OF SAMPLES

(75) Inventors: Brendon Francis Conlan, Lane Cove (AU); Andrew Mark Gilbert, Eastwood (AU); Chenicheri Hariharan Nair, Homebush Bay (AU); Lucy Jane Ryan, Baulkham Hills (AU); Dennis Brian Rylatt, Ryde (AU); Theresa Marie Thomas, Schofields (AU)

(73) Assignee: Gradipore, Limited, Frenchs Forest (AU)

( * ) Notice: Subject to any disclaimer, the term of this patent is extended or adjusted under 35 U.S.C. 154(b) by 152 days.

(21) Appl. No.: 09/837,677

(22) Filed: Apr. 18, 2001

(65) Prior Publication Data

US 2001/0053537 A1 Dec. 20, 2001

(30) Foreign Application Priority Data

Apr. 18, 2000 (AU) .............................................. PQ6974
Jul. 26, 2000 (AU) .............................................. PQ9013

(51) Int. Cl.⁷ ...................... G01N 27/447; G01N 27/453
(52) U.S. Cl. ...................... 204/456; 204/450; 204/600; 204/606
(58) Field of Search ................................ 204/450, 456, 204/462, 465, 467, 466, 522, 523, 527, 528, 600, 606, 615, 618, 633, 634

(56) References Cited

U.S. PATENT DOCUMENTS

| | | |
|---|---|---|
| 3,878,564 A | 4/1975 | Yao et al. |
| 4,036,748 A | 7/1977 | Knickel et al. |
| 4,045,337 A | 8/1977 | Knickel et al. |
| 4,045,455 A | 8/1977 | Vogel |
| 4,069,215 A | 1/1978 | Elfert et al. |
| 4,115,225 A | 9/1978 | Parsi |
| 4,123,342 A | 10/1978 | Ahlgren |
| 4,174,439 A | 11/1979 | Rauenbusch et al. |
| 4,196,304 A | 4/1980 | Naumann |
| 4,204,929 A | 5/1980 | Bier |
| 4,217,227 A | 8/1980 | Elfert et al. |
| 4,238,306 A | 12/1980 | Perry et al. |
| 4,238,307 A | 12/1980 | Perry et al. |
| 4,252,652 A | 2/1981 | Elfert et al. |
| 4,259,079 A | 3/1981 | Blum |
| 4,269,967 A | 5/1981 | Elfert et al. |
| 4,276,140 A | 6/1981 | Jain |
| 4,279,724 A | 7/1981 | Hearn et al. |
| 4,299,677 A | 11/1981 | Venkatasubramanian et al. |
| 4,322,275 A | 3/1982 | Jain |
| 4,362,612 A | 12/1982 | Bier |
| 4,376,023 A | 3/1983 | Venkatsubramanian et al. |
| 4,381,232 A | 4/1983 | Brown |
| 4,383,923 A | 5/1983 | Elfert |
| 4,396,477 A | 8/1983 | Jain |

(List continued on next page.)

FOREIGN PATENT DOCUMENTS

| | | |
|---|---|---|
| GB | 2 118 975 A | 2/1983 |
| WO | WO 97/14486 | 4/1997 |
| WO | WO 98/21384 | 5/1998 |
| WO | WO 98/43718 | 10/1998 |

Primary Examiner—Alex Noguerola
(74) Attorney, Agent, or Firm—Baker & McKenzie

(57) ABSTRACT

A system for separating biomolecules by electrophoretic separation including a first separation barrier having a defined molecular mass cut-off disposed in the first electric field area, a first restriction barrier disposed between a first cathode zone and a first separation barrier so as to define a first interstitial volume therebetween, a second restriction barrier disposed between the first anode zone and the first separation barrier so as to define a second interstitial volume therebetween, and a pumping means to provide a sample constituent in a selected one of the first interstitial and second interstitial volumes wherein upon application of the first voltage potential, a selected separation product is removed from the sample constituent through the first separation barrier and provided to the other of the first and second interstitial volumes.

17 Claims, 5 Drawing Sheets

U.S. PATENT DOCUMENTS

| | | |
|---|---|---|
| 4,441,978 A | 4/1984 | Jain |
| 4,533,447 A | 8/1985 | Meldon |
| 4,608,140 A | 8/1986 | Goldstein |
| 4,661,224 A | 4/1987 | Goldstein et al. |
| 4,673,483 A | 6/1987 | Mandle |
| 4,711,722 A | 12/1987 | Toyoshi et al. |
| 4,746,647 A | 5/1988 | Svenson |
| 4,749,458 A | 6/1988 | Muroi et al. ............ 204/182.3 |
| 4,780,411 A | 10/1988 | Piejko et al. |
| 4,897,169 A | 1/1990 | Bier et al. |
| 4,963,236 A | 10/1990 | Rodkey et al. |
| 5,043,048 A | 8/1991 | Muralidhara |
| 5,080,770 A | 1/1992 | Culkin |
| 5,082,548 A | 1/1992 | Faupel et al. |
| 5,087,338 A | 2/1992 | Perry et al. |
| 5,096,547 A | 3/1992 | Klotz et al. |
| 5,114,555 A | 5/1992 | Stimpson |
| 5,127,999 A | 7/1992 | Klotz et al. |
| 5,160,594 A | 11/1992 | Huff et al. |
| 5,173,164 A | 12/1992 | Egen et al. |
| 5,185,086 A | 2/1993 | Kaali et al. |
| 5,238,570 A | 8/1993 | Hugl et al. |
| 5,277,774 A | 1/1994 | Shmidt et al. |
| 5,336,387 A | 8/1994 | Egen et al. |
| 5,340,449 A | 8/1994 | Shukla |
| 5,352,343 A | 10/1994 | Bailes et al. |
| 5,407,553 A | 4/1995 | Herron et al. |
| 5,420,047 A | 5/1995 | Brandt et al. |
| 5,437,774 A | 8/1995 | Lautsen |
| 5,441,646 A | 8/1995 | Heller et al. |
| 5,490,939 A | 2/1996 | Gerigk et al. |
| 5,503,744 A | 4/1996 | Ikematsu et al. |
| 5,504,239 A | 4/1996 | Mehl et al. |
| 5,558,753 A | 9/1996 | Gallagher et al. |
| 5,561,115 A | 10/1996 | Tenold |
| 5,565,102 A | 10/1996 | Brandt et al. |
| 5,610,285 A | 3/1997 | Lebing et al. |
| 5,662,813 A | 9/1997 | Sammons et al. |
| 5,723,031 A | 3/1998 | Durr et al. |
| 5,733,442 A | 3/1998 | Shukla |
| 5,736,023 A | 4/1998 | Gallagher et al. |
| 5,868,938 A | 2/1999 | Bomer et al. |
| 5,891,736 A | 4/1999 | Chapoteau et al. |
| 5,906,724 A | 5/1999 | Sammons et al. |
| 5,938,904 A | 8/1999 | Bader et al. |
| 5,986,075 A | 11/1999 | DuBose et al. |
| 6,093,296 A | 7/2000 | Soane et al. |
| 6,117,297 A | 9/2000 | Goldstein |
| 6,129,842 A | 10/2000 | Kostanian |
| 6,171,825 B1 | 1/2001 | Chan et al. |

Figure 1

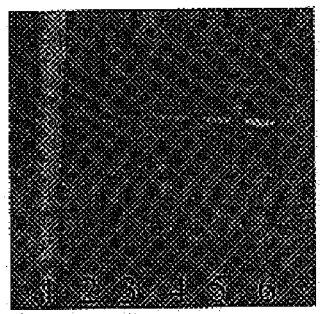

Lane 1: Sigma molecular weight markers
Lane 2: B/S time 0
Lane 3: B/S time 60
Lane 4: B/S time 120
Lane 5: B/S time 180
Lane 6: B/S time 270

Figure 2

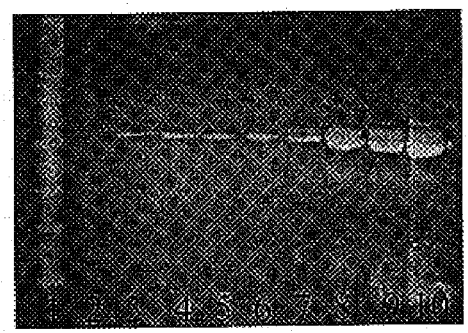

Lane 1: Sigma molecular weight markers.
Lane 2: B/S time 0 of albumin separation.
Lane 3: B/S time 60 of albumin separation.
Lane 4: B/S time 120 of albumin separation.
Lane 5: B/S time 180 of albumin separation.
Lane 6: B/S time 270 of albumin separation
Lane 7: D/S time 60.
Lane 8: D/S time 120.
Lane 9: D/S time 180.
Lane 10: D/S time 270.

Lane 1: Sigma molecular weight markers.
Lane 2: B/S time 0 of albumin separation.
Lane 3: B/S time 150 of albumin separation.
Lane 4: B/S time 270 of albumin separation.
Lane 5: B/S after 1$^{st}$ pass of buffer reclamation.
Lane 6: B/S after 2$^{nd}$ pass.
Lane 7: D/S after 1$^{st}$ pass.
Lane 8: D/S after 2$^{nd}$ pass.
Lane 9: D/S after 3$^{rd}$ pass.

Albumin Purification         Buffer Reclamation

Lane 1: Markers
Lane 2: U/S0
Lane 3: U/S90
Lane 4: U/S270
Lane 5: D/S0
Lane 6: D/S150
Lane 7: D/S 210
Lane 8: D/S 270

ELECTROPHORESIS SEPARATION AND TREATMENT OF SAMPLES

BACKGROUND OF THE INVENTION

The present invention relates to apparatus and methods for processing or separating compounds, particularly biomolecules in the form of recombinant proteins produced by recombinant microorganisms and the removal of small molecular mass macromolecules from solutions.

Processing solutions of biomolecules often involves the use of various buffer solutions. During commercial processing of biomolecules for example, large volumes of buffers are required which can be costly and also may cause problems for disposal. Often, spent buffers contain macromolecular waste materials which not only prevent further use of the buffers but also need to be disposed of safely.

In the past, a preparative electrophoresis technology for macromolecule separation which utilises tangential flow across a polyacrylamide membrane when a charge is applied across the membrane was used to separate macromolecules. The general design of the earlier system facilitated the purification of proteins and other macromolecules under near native conditions. The technology is bundled into a cartridge comprising several membranes housed in a system of specially engineered grids and gaskets which allow separation of macromolecules by charge and/or molecular weight. The system can also concentrate and desalt/dialyse at the same time. The multi-modal nature of the system allows this technology to be used in a number of other areas especially in the production of biological components for medical use.

The effect of low molecular weight proteins and ions building up in the buffer stream can slow the transfer of proteins during purification. These contaminants carry current which lessens target protein migration and can lead to heat build up in the protein solution. There is a need to be able to remove contaminants from the buffers streams in such electrophoretic systems.

It has been discovered that the buffer stream can be processed to remove these low molecular weight contaminants. By cycling the buffer stream through a separate apparatus, it is possible to remove the majority of the proteins/contaminants present in the buffer stream whilst maintaining the conductivity and pH of the buffer.

The modern biotechnology industry is faced with a number of problems especially concerning the processing of biomolecules produced recombinantly. Expression of recombinant genes in recombinant cells is often low and purification from the host cell difficult. The starting sample is usually dilute and the need to concentrate the sample by conventional means can give low recoveries. Usually, a flag peptide attached to the recombinant protein is used (often a six histidine peptide is added to the protein) to enable purification of the protein. This tag can interfere with the biological function by effecting folding for example, leading to inactive protein and incorrect assessment of the construct.

Presently, the purification of biomolecules, particularly recombinant proteins is sometimes a long and cumbersome process especially when purifying recombinant biomolecules.

It is desirable to have a preparative electrophoretic system which can efficiently and effectively separate macromolecules, such as recombinant proteins, and can remove contaminants from product samples and buffer streams.

SUMMARY OF THE INVENTION

In accordance with the present invention, there is provided an electrophoretic system which efficiently and effectively separates macromolecules and can remove contaminants from samples and buffer streams.

Further, in accordance with the present invention, there is provided an apparatus for separating macromolecules by electrophoretic separation, the apparatus comprising:

(a) a first cathode in a first cathode zone;

(b) a first anode in a first anode zone, the anode disposed relative to the first cathode so as to be adapted to generate a first electric field in a first electric field area therebetween upon application of a first voltage potential between the first cathode and the first anode;

(c) a first electrophoretic buffer disposed in the first cathode zone and the first anode zone;

(d) a first separation membrane having a defined molecular mass cut-off disposed in the first electric field area;

(e) a first restriction membrane disposed between the first cathode zone and the first separation membrane so as to define a first interstitial volume therebetween;

(f) a second restriction membrane disposed between the first anode zone and the first separation membrane so as to define a second interstitial volume therebetween;

(g) means adapted to provide a sample constituent in a selected one of the first interstitial and second interstitial volumes wherein upon application of the first voltage potential, a selected separation product is removed from the sample constituent through the first separation membrane and provided to the other of the first and second interstitial volumes;

(h) a second cathode zone optionally containing a second anode;

(i) a second anode zone optionally containing a second anode, the second anode zone disposed relative to the second cathode zone so as to be adapted to generate a second electric field area therebetween upon application of an optional second voltage potential between the optional second cathode and the optional second anode;

(j) a second electrophoretic buffer disposed in the second anode zone and the second cathode zone;

(k) a second separation membrane having a defined molecular mass cut-off disposed in the second electric field area;

(l) a third restriction membrane disposed between the second anode zone and the second separation membrane so as to define a third interstitial volume therebetween;

(m) a fourth restriction membrane disposed between the second cathode zone and the second separation membrane so as to define a fourth interstitial volume therebetween;

(n) means adapted to provide the first electrophoretic buffer to a selected one of the third and fourth interstitial volumes wherein a selected separation product is removed from the first electrophoretic buffer through the second separation membrane, and provided to the other of the third and fourth interstitial volumes while substantially preventing the first electrophoretic buffer from entering the other of the third and fourth interstitial volumes; and (o) means adapted to provide the first electrophoretic buffer after the selected separation product has been removed from the first electrophoretic buffer to a selected one of the first cathode and anode zones.

Still further, in accordance with the present invention, there is provided in a first general aspect, a system for separating macromolecules by electrophoresis, the system comprising:

(a) a first cathode compartment and a first anode compartment;

(b) a first cathode and first anode positioned in the respective compartments;

(c) a first electrophoresis buffer stream feeding the first cathode and first anode compartments;

(d) a first chamber and a second chamber positioned on either side of a first ion-permeable separation membrane having a defined molecular mass cut-off, the first chamber and the second chamber being positioned between the cathode and the anode compartments and separated by an ion-permeable restriction membrane positioned on each side of the separation membrane, the restriction membrane allowing flow of ions into and out of the compartments and chambers under the influence of an electric field but substantially restrict movement of at least one macromolecule type from the second chamber into a compartment;

(e) a second cathode compartment and a second anode compartment;

(f) optionally, a second cathode and second anode positioned in the respective second cathode and anode compartments;

(g) a second electrophoresis buffer stream feeding the second cathode and second anode compartments;

(h) a third chamber and a fourth chamber positioned on either side of a second ion-permeable separation membrane having a defined molecular mass cut-off, the third chamber and the fourth chamber being positioned between the second cathode and the second anode compartments and separated by third and fourth ion-permeable restriction membranes positioned on each side of the second separation membrane.

An advantage of the present invention is that the electrophoretic system which efficiently and effectively separates macromolecules and can remove contaminants from samples and buffer streams.

Another advantage of the present invention is that recombinant molecules do not require a flag peptide (or peptide tag in general) for its purification. Removing the requirement of a flag/tag on recombinant molecules eliminates the potential of the flag/tag region to interfere with biological function of the molecule. Therefore flag/tag sequences are not required in the vector of the cloned recombinant molecule.

Another advantage is that the electrophoretic separation method of the present invention can result in yields of greater than about 70% with purity at least about 90%.

Still another advantage is that the electrophoretic separation method of the present invention is able to be scaled-up without denaturing or adversely altering the physical or biological properties of recombinant proteins separated by the present invention.

These and other advantages and benefits of the invention will be apparent to those skilled in the art upon reading and understanding of the following detailed description.

BRIEF DESCRIPTION OF THE DRAWINGS

FIG. 1 shows an SDS-PAGE gel showing the gradual build up of protein in the buffer stream during an albumin separation using the present invention. Lane 1: Sigma molecular weight markers. Lane 2: B/S (buffer stream) time 0 min. Lane 3: B/S time 60 min. Lane 4: B/S time 120 min. Lane 5: B/S time 180 min. Lane 6: B/S time 270 min.

FIG. 2 shows an SDS-PAGE gel showing the gradual build up of protein in the buffer stream during an albumin separation using the present invention. Lane 1: Sigma molecular weight markers. Lane 2: B/S (buffer stream) time 0 of albumin separation. Lane 3: B/S time 60 of albumin separation. Lane 4: B/S time 120 of albumin separation. Lane 5: B/S time 180 of albumin separation. Lane 6: B/S time 270 of albumin separation. Lane 7: D/S (down stream) time 60 min. Lane 8: D/S time 120 min. Lane 9: D/S time 180 min. Lane 10: D/S time 270 min.

DETAILED DESCRIPTION OF THE INVENTION

Figure 3:
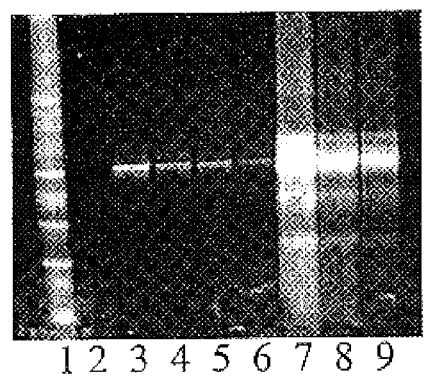
FIG. 3 shows an SDS-PAGE gel stained with Sypro ruby (BioRad) showing the amount of protein present in the buffer stream during an albumin separation and the amount of protein removed using the buffer reclamation protocol. A separation was carried out using a 200 kDa separation membrane with 50 kDa restriction membranes from 15 mL of straight plasma for 150 minutes then the cartridge was changed and the same run again completed. The buffer was not changed between the two experiments. The contaminated buffer was then cleaned by running it through the present invention in a single pass fashion with a 1.5 kDa separation membrane and 5 kDa restriction membranes. Lane 1: Sigma molecular weight markers. Lane 2: B/S (buffer stream) time 0 of albumin separation. Lane 3: B/S time 150 min of albumin separation. Lane 4: B/S time 270 min of albumin separation. Lane 5: B/S after $1^{st}$ pass of buffer reclamation. Lane 6: B/S after $2^{nd}$ pass. Lane 7: D/S after $1^{st}$ pass. Lane 8: D/S after $2^{nd}$ pass. Lane 9: D/S after $3^{rd}$ pass.

The present invention is directed to a system or apparatus for separating macromolecules by electrophoretic separation, the apparatus comprising:

(a) a first cathode in a first cathode zone;

(b) a first anode in a first anode zone, the anode disposed relative to the first cathode so as to be adapted to generate a first electric field in a first electric field area therebetween upon application of a first voltage potential between the first cathode and the first anode;

(c) a first electrophoretic buffer disposed in the first cathode zone and the first anode zone;

(d) a first separation membrane having a defined molecular mass cut-off disposed in the first electric field area;

(e) a first restriction membrane disposed between the first cathode zone and the first separation membrane so as to define a first interstitial volume therebetween;

(f) a second restriction membrane disposed between the first anode zone and the first separation membrane so as to define a second interstitial volume therebetween;

(g) means adapted to provide a sample constituent in a selected one of the first interstitial and second interstitial volumes wherein upon application of the first voltage potential, a selected separation product is removed from the sample constituent through the first separation membrane and provided to the other of the first and second interstitial volumes;

(h) a second cathode zone optionally containing a second cathode;

(i) a second anode zone optionally containing a second anode, the second cathode zone disposed relative to the second anode zone so as to be adapted to generate a second electric field area therebetween upon application of an optional second voltage potential between the optional second cathode and the optional second anode;

(j) a second electrophoretic buffer disposed in the second cathode zone and the second anode zone;

(k) a second separation membrane having a defined molecular mass cut-off disposed in the second electric field area;

(l) a third restriction membrane disposed between the second cathode zone and the second separation membrane so as to define a third interstitial volume therebetween;

(m) a fourth restriction membrane disposed between the second anode zone and the second separation membrane so as to define a fourth interstitial volume therebetween;

(n) means adapted to provide the first electrophoretic buffer to a selected one of the third and fourth interstitial volumes wherein a selected separation product is removed from the first electrophoretic buffer through the second separation membrane, and provided to the other of the third and fourth interstitial volumes while substantially preventing the first electrophoretic buffer from entering the other of the third and fourth interstitial volumes; and (o) means adapted to provide the first electrophoretic buffer after the selected separation product has been removed from the first electrophoretic buffer to a selected one of the first interstitial volumes and the first cathode and anode zones.

Preferably, the apparatus contains the optional second cathode and anode and step (n) is carried out upon application of a second electric potential.

Preferably, the second cathode, second cathode zone, second anode, second anode zone, and the second electrophoretic buffer are contiguously disposed in a secondary separation system.

Preferably, the first and second interstitial volumes are provided as a cartridge positioned between the first cathode zone and the first anode zone forming first upstream and downstream interstitial volumes.

Preferably, the third and fourth interstitial volumes are provided as a cartridge positioned between the second cathode zone and the second anode zone forming second upstream and downstream interstitial volumes.

More particularly, in a first embodiment, the present invention is directed a system for separating macromolecules by electrophoresis, the system comprising:

(a) a first cathode compartment and a first anode compartment;

(b) a first cathode and first anode positioned in the respective compartments;

(c) a first electrophoresis buffer stream feeding the first cathode and first anode compartments;

(d) a first chamber and a second chamber positioned on either side of a first ion-permeable separation membrane having a defined molecular mass cut-off, the first chamber and the second chamber being positioned between the cathode and the anode compartments and separated by an ion-permeable restriction membrane positioned on each side of the separation membrane, the restriction membrane allowing flow of ions into and out of the compartments and chambers under the influence of an electric field but substantially restrict movement of at least one macromolecule type from the second chamber into a compartment;

(e) a second cathode compartment and a second anode compartment;

(f) optionally, a second cathode and second anode positioned in the respective second cathode and second anode compartments;

(g) a second electrophoresis buffer stream feeding the second cathode and second anode compartments;

(h) a third chamber and a fourth chamber positioned on either side of a second ion-permeable separation membrane having a defined molecular mass cut-off, the third chamber and the fourth chamber being positioned between the second cathode and the second anode compartments and separated by third and fourth ion-permeable restriction membranes positioned on each side of the second separation membrane.

The cathode zones or compartments and the anode zones or compartments are supplied with suitable buffer solutions by any suitable means. A mixture comprising compounds to be processed is supplied directly to the first or second interstitial volumes or chambers by any suitable means.

Preferably, the zones or compartments and the interstitial volumes or chambers are configured to allow flow of the respective buffer and sample solutions forming streams. In this form, large volumes can be processed quickly and efficiently. The solutions are typically moved or recirculated through the zones or compartments and chambers from respective reservoirs by pumping means. In a preferred embodiment, peristaltic pumps are used as the pumping means for moving the sample, buffers or fluids.

In one embodiment, the buffer, sample or product solutions are cooled by any suitable means to ensure no inactivation of the micromolecules, compounds or macromolecules occurs during the separation process and to maintained a desired temperature of the apparatus while in use.

Preferably, in order to collect and concentrate the separated compounds or macromolecules, solution in at least one of the chambers or streams containing any separated compounds or macromolecules is collected and replaced with suitable solvent to ensure that electrophoresis can continue.

In use, a sample is placed in the first chamber, an electric potential is applied between the first and second chambers causing movement of any small macromolecules in the sample to the first electrophoresis buffer stream, passing buffer containing the small macromolecules in the first electrophoresis buffer stream to the third chamber, optionally applying an electric potential between the third chamber and fourth chamber, allowing movement of small macromolecules through the second separation membrane to the fourth chamber while substantially preventing the buffer in the third chamber from passing to the fourth chamber, and returning buffer from the third chamber to the first electrophoresis buffer stream.

It will be appreciated that the order of chambers are suitably reversed where buffer containing the small macromolecules in the first electrophoresis buffer stream is passed to the fourth chamber, optionally applying an electric potential between the third chamber and fourth chamber, allowing movement of small macromolecules through the second separation membrane to the third chamber while substantially preventing the buffer in the fourth chamber from passing to the third chamber, and returning buffer from the fourth chamber to the first electrophoresis buffer stream.

The ion-permeable separation membranes or barriers are preferably electrophoresis separation membranes made from polyacrylamide and having a molecule mass cut-off from about 1 kDa to about 1500 kDa. The selection of the molecular mass cut-off of the separation membranes will depend on the sample being processed and the other molecules in the mixture. It will be appreciated, however, that other membrane chemistries or constituents are suitably used for the present invention.

The first and second restriction membranes or barriers are preferably restriction membranes formed from polyacrylamide and having a molecular mass cut-off less than the separation membrane, preferably from about 1 kDa to about 100 kDa. The selection of the molecular mass cut-off of the restriction membranes will depend on the sample being processed and the size of the small macromolecules to be removed.

In one preferred form, the first and second chambers and the third and fourth chambers are provided as separate cartridges or cassettes positioned between the respective electrode compartments forming an upstream and downstream chamber which define the first and second chambers and third and fourth chambers. The configuration of the cartridges is preferably a housing with a electrophoresis separation membrane positioned between two restriction membranes thus forming the required chambers.

Preferably, the cartridge or cassette is removable from an apparatus adapted to contain the cartridge.

A molecular mass cut-off of about 1000 kDa has been found to be particularly suitable for the first ion-permeable separation membrane, which is preferably an electrophoresis separation membrane. This cut-off prevents the movement of buffer but allows movement of macromolecules to the second chamber where they are held by the second restriction membrane. It will be appreciated, however, that other cut-off membranes that prevent the movement of small macromolecules would also be suitable. In a preferred form, the electrophoresis separation membrane forms part of a separation cartridge where two restriction membranes having molecular mass cut-offs of about 5 kDa are positioned and spaced either side of the second electrophoresis separation membrane thus forming the third and fourth chambers.

The distance between the electrodes has an effect on the separation or movement of macromolecules through the membranes. It has been found that the shorter the distance between the electrodes, the faster the electrophoretic movement of macromolecules. A distance of about 6 cm has been found to be suitable for a laboratory scale apparatus. For scale up versions, the distance will depend on the number and type of separation membranes, the size and volume of the chambers for samples, buffers and separated products. Preferred distances would be in the order of about 6 mm to about 10 mm. The distance will also relate to the voltage applied to the apparatus. The effect of the electric field is based on the equation:

$$e = V/d$$

(e=electric field, V=voltage, d=distance)

Therefore, the smaller the distance between the electrodes the faster the separation. Preferably, the distance between the electrodes should decrease in order to increase electric field strength, thereby further improving transfer rates.

Flow rate of sample/buffer has an influence on the separation of macromolecules. Rates of milliliters per hour up to liters per hour are used depending on the configuration of the apparatus and the sample to be separated. Currently in a laboratory scale instrument, the preferred flow rate is about 20±5 mL/min. However, flow rates ranging from about 0 mL/min to about 50,000 mL/min are used across the various separation regimes. The maximum flow rate is even higher, depending on the pumping means and size of the apparatus. The selection of the flow rate is dependent on the product to be transferred, efficiency of transfer, pre- and post-positioning with other applications.

Selection or application of the voltage and/or current applied varies depending on the separation. Typically up to several thousand volts are used but choice and variation of voltage will depend on the configuration of the apparatus, buffers and the sample to be separated. In a laboratory scale instrument, the preferred voltage is about 250 V. However, depending on transfer, efficiency, scale-up and particular method from about 0 V to about 5000 V are used. Higher voltages are also considered, depending on the apparatus and sample to be treated.

In one embodiment, a number of first and second chambers are stacked in the one apparatus for use in a scale-up device.

In a second aspect, the present invention provides a method for removing small macromolecules from a sample constituent, the method comprising:

(a) providing an electrophoretic apparatus according to the first aspect of the present invention;

(b) adding the sample constituent to the first interstitial volume;

(c) applying a first voltage potential between the first and second interstitial volumes wherein upon application of the first voltage potential, a selected separation product is removed from the sample constituent through the first separation membrane and provided to the other of the first and second interstitial volumes and the first electrophoretic buffer;

(d) passing the first electrophoretic buffer containing the small macromolecules to a selected one of the third and fourth interstitial volumes;

(e) allowing movement of small macromolecule contaminants through the second ion-permeable separation membrane to the other of the third and fourth interstitial volumes while substantially preventing the buffer from passing to the such interstitial volume;

(f) optionally applying a second voltage potential between the third and fourth interstitial volumes to assist step (e); and (g) returning the first electrophoretic buffer after the selected separation product has been removed from the first electrophoretic buffer to a selected one of the first cathode and first anode zones.

In a preferred embodiment of the second aspect of the present invention, the method further comprises:

(h) periodically stopping and reversing the first voltage potential between the first and second chambers to cause movement of any macromolecules other than the small macromolecules to be removed from the sample having entered the first ion-permeable separation membrane to move back into the first chamber, wherein substantially not allowing any small macromolecules, or other macromolecules that have entered the second chamber to re-enter first chamber.

Reversal of current is an option but another alternative is a resting period. Resting (a period without an electric potential being applied, but pumps remain on) is an optional step that either replaces or is included before or after an optional voltage potential reversal. This reversal technique is often practised for protein separation work as an alternative to reversing the potential.

One benefit of the method according to the present invention is the possibility of scale-up without denaturing or adversely altering the physical or biological properties of compounds to be separated.

Preferably, the sample contains other macromolecules which are also separated from the first chamber by size and charge by the first ion-permeable separation membrane to the second chamber.

The sample is any suitable sample which contains small macromolecules that need to be removed. The small macromolecules are usually contaminants with other macromolecules that need to be purified or separated. Examples include, but not limited to, blood-derived products such as plasma, antibody samples, samples containing biomolecules such as proteins, peptides, glycoproteins, oligonucleotides, recombinant proteins, cell extracts, cell culture supernatant, growth factors, antigens, immunogens, and combinations thereof.

Small macromolecules include but not limited to proteins, peptides, protein fragments contaminating solutions of macromolecules, and combinations thereof. Typically, the small macromolecules have a molecular mass of between from about 100 Da and about 100 kDa.

Preferably, the buffer is recirculated between the first electrophoresis buffer stream to the third chamber and from the third chamber back to the first electrophoresis buffer stream. In this situation, simultaneous separation of macromolecules is achieved while removing small macromolecules and ions from the first buffer stream. Solutes, salts and ions in the first electrophoresis buffer stream are removed to the second buffer stream by movement through the second restriction membranes. The second buffer stream is preferably the same buffer type as that used in the first chamber.

Alternatively, the buffer is recirculated between the first electrophoresis buffer stream to the fourth chamber and from the fourth chamber back to the first electrophoresis buffer stream. In this situation, simultaneous separation of macromolecules is achieved while removing small macromolecules and ions from the first buffer stream. Solutes, salts and ions in the first electrophoresis buffer stream are removed to the second buffer stream by movement through the second restriction membranes. The second buffer stream is preferably the same buffer type as that used in the first chamber.

During step (e), the small macromolecules move through the first ion-permeable separation membrane, and/or the first restriction membranes then may move into the first buffer stream through the second restriction membrane.

In a third aspect, the present invention provides use of the apparatus according to the first aspect of the present invention in the separation of one or more biomolecules, particularly recombinant molecules from a sample.

In a fourth aspect, the present invention provides a recombinant protein produced by the method according to the second aspect of the present invention.

Preferably, the recombinant protein is obtained with at least about 70% purity and at least about 70% recovery from the starting sample. More preferably, the recombinant protein is obtained with at least about 80% purity and at least about 80% recovery from the starting sample. Even more preferably, the recombinant protein is obtained with at least about 90% purity and at least about 90% recovery from the starting sample.

The recombinant protein is any recombinant molecule produced from a eukaryotic and/or prokaryotic system (media, culture, supernatant or cell lysate).

In a fifth aspect, the present invention provides a method of separating a recombinant protein from a mixture of compounds, the method comprising:

(a) placing the mixture into a selected one of a first interstitial volume and a second interstitial volume, wherein the interstitial volumes are separated by an ion-permeable separation membrane having a molecular mass cut-off less than or greater than the molecular mass of the recombinant protein and wherein the first and second interstitial volumes being separated from an electrophoresis buffer stream by ion-permeable restriction membranes configured to allow the movement of ions and small macromolecules during application of a electric potential but prevent the movement of the recombinant protein, wherein the interstitial volumes are positioned between a cathode in a cathode zone and an anode in an anode zone, the anode disposed relative to the cathode so as to be adapted to generate an electric field in a electric field area therebetween upon application of a voltage potential between the cathode and the anode;

(b) selecting a solvent for the selected one of the first interstitial and second interstitial volumes having a pH such that the recombinant protein or other compounds in the sample have a desired charge;

(c) applying a voltage potential between the first interstitial and second interstitial volumes, wherein upon application of the voltage potential, selected compounds or the recombinant protein in the mixture are caused to move through the first separation membrane and provided to the other of the first interstitial and second interstitial volumes;

(d) optionally, periodically stopping and reversing the first voltage potential to cause movement of the selected compounds or the recombinant protein having entered the separation membrane to move back into the interstitial volume from which selected compounds or recombinant protein have been removed, wherein substantially not allowing any of the selected compounds or recombinant protein that have been provided to the other of the first interstitial and second interstitial volumes to re-enter the interstitial volume from which such selected compounds or recombinant protein have been removed; and (e) maintaining steps (c) and optionally (d) until the recombinant protein is obtained with at least about 70% purity and at least about 70% recovery from the starting mixture.

Preferably, the pH of the solvent or buffer in the first interstitial volume is either greater than the pI (isoelectric point) of the recombinant protein such that the recombinant protein is negatively charged or less than the pI of the recombinant protein such that the recombinant protein is positively charged.

More particularly, in one preferred from, the method comprises:

(a) placing the mixture in a sample stream, the sample stream being separated from a product stream by an ion-permeable separation membrane having a molecular mass cut-off less than the molecular mass of the recombinant protein; the sample and product streams being separated from an electrophoresis buffer stream by ion-permeable restriction membranes configured to allow the movement of ions and small macromolecules during application of a voltage potential, the sample and product streams are positioned between a cathode in a cathode zone and an anode in an anode zone, the anode disposed relative to the cathode so as to be adapted to generate an electric field in a electric field area therebetween upon application of a voltage potential between the cathode and the anode;

(b) selecting a buffer or solvent for the sample stream having a pH such that the recombinant protein or other compounds in the sample have a desired charge;

(c) applying a first voltage potential between the sample and product streams causing movement of compounds in the mixture having a molecular mass less than the recombinant protein through the separation membrane into the product stream while the recombinant protein is substantially retained in the sample stream, or if entering the separation membrane, being substantially prevented from passing through the separation membrane;

(d) optionally, periodically stopping and reversing the first voltage potential to cause movement of the recombinant protein having entered the separation membrane to move back into the sample stream, wherein substantially not causing any compounds that have entered the product stream to re-enter sample stream; and (e) maintaining steps (c) and optionally (d) until the desired amount of compounds having a molecular mass less than the recombinant protein have been removed from the mixture in the sample stream, wherein the recombinant protein in the sample obtained has at least about 70% purity and at least about 70% recovery from the starting mixture.

Preferably, the pH of the solvent or buffer in the sample stream is greater than the pI of the other compounds such that the compounds are negatively charged.

More particularly, in another preferred from, the method comprises:

(a) placing the mixture into a selected one of a first interstitial volume and a second interstitial volume, wherein the interstitial volumes are separated by an ion-permeable separation membrane having a molecular mass cut-off greater than the molecular mass of the recombinant protein and wherein the first and second interstitial volumes being separated from an electrophoresis buffer stream by ion-permeable restriction membranes configured to allow the movement of ions and small macromolecules during application of a voltage potential, the interstitial volumes are positioned between a cathode in a cathode zone and an anode in an anode zone, the anode disposed relative to the cathode so as to be adapted to generate an electric field in a electric field area therebetween upon application of a voltage potential between the cathode and the anode;

(b) selecting a solvent for the selected one of the first interstitial and second interstitial volumes having a pH such that the recombinant protein or other compounds in the sample have a desired charge;

(c) applying a first voltage potential between the first interstitial and second interstitial volumes, wherein upon application of the first voltage potential, the recombinant protein is removed from the mixture through the first separation membrane and provided to the other of the first interstitial and second interstitial volumes and wherein the remaining compounds are substantially retained in the interstitial volume from which the recombinant protein has been removed, or if entering the separation membrane, being substantially prevented from passing through the separation membrane;

(d) optionally, periodically stopping and reversing the first voltage potential to cause movement of the remaining compounds which have entered the separation membrane to move back into the interstitial volume from the recombinant protein has been removed, wherein substantially not allowing any of the recombinant protein that has been provided to the other of the first interstitial and second interstitial volumes to re-enter the interstitial volume from which the recombinant protein has been removed; and (e) maintaining steps (c) and optionally (d) until the desired amount of recombinant protein has been removed from the mixture, wherein the recombinant protein obtained has at least about 70% purity and at least about 70% recovery from the starting mixture.

Preferably, the pH of the solvent or buffer in the first interstitial volume is greater than the pI of the recombinant protein such that the recombinant protein is negatively charged.

In a sixth aspect, the present invention provides a method of separating a recombinant protein from a mixture of compounds, the method comprising:

(a) placing the mixture into a selected one of a first interstitial volume and a second interstitial volume, wherein the interstitial volumes are separated by a first ion-permeable separation membrane having a molecular mass cut-off less than the molecular mass of the recombinant protein and wherein the first and second interstitial volumes being separated from a first electrophoresis buffer stream by a first and second ion-permeable restriction membrane configured to allow the movement of ions and small macromolecules during application of a voltage potential, the first and second interstitial volumes are positioned between a first cathode in a first cathode zone and a first anode in a first anode zone, the first anode disposed relative to the first cathode so as to be adapted to generate an electric field in a first electric field area therebetween upon application of a voltage potential between the first cathode and the first anode;

(b) selecting a solvent for the selected one of the first interstitial and second interstitial volumes having a pH such that the recombinant protein or other compounds in the sample have a desired charge;

(c) applying a first voltage potential between the first interstitial and second interstitial volumes, wherein upon application of the first voltage potential, selected compounds in the mixture having a molecular mass less than the recombinant protein are removed from the mixture through the first separation membrane and provided to the other of the first interstitial and second interstitial volumes and wherein the recombinant protein is substantially retained in the interstitial volume from which the selected compounds have been removed, or if entering the first separation membrane, being substantially prevented from passing through the first separation membrane;

(d) optionally, periodically stopping and reversing the first voltage potential to cause movement of the recombinant protein having entered the first separation membrane to move back into the interstitial volume from which selected compounds have been removed, wherein substantially not allowing any of the selected compounds that have been provided to the other of the first interstitial and second interstitial volumes to re-enter the interstitial volume from which such selected compounds have been removed;

(e) maintaining steps (c) and optionally (d) until the desired amount of selected compounds have been removed from the mixture;

(f) placing the mixture obtained in step (e) into a selected one of a third interstitial volume and a fourth interstitial volume, wherein the interstitial volumes are separated by a second ion-permeable separation membrane having a molecular mass cut-off greater than the molecular mass of the recombinant protein and wherein the third and fourth interstitial volumes being separated from a second electrophoresis buffer stream by third and fourth ion-permeable restriction membranes configured to allow the movement of ions and small macromolecules during application of a voltage potential, the third and fourth interstitial volumes are positioned between a second cathode in a second cathode zone and a second anode in a second anode zone, the second anode disposed relative to the second cathode so as to be adapted to generate an electric field in a second electric field area therebetween upon application of a voltage potential between the second cathode and the second anode;

(g) selecting a solvent for the selected one of the third interstitial and fourth interstitial volumes having a pH such that the recombinant protein or other compounds in the sample have a desired charge;

(h) applying a second voltage potential between the third interstitial and fourth interstitial volumes, wherein upon application of the second voltage potential, the recombinant protein is removed from the mixture through the second separation membrane and provided to the other of the third interstitial and fourth interstitial volumes and wherein the remaining compounds are substantially retained in the interstitial volume from which the recombinant protein has been removed, or if entering the second separation membrane, being substantially prevented from passing through the second separation membrane;

(i) optionally, periodically stopping and reversing the second voltage potential to cause movement of the remaining compounds which have entered the second separation membrane to move back into the interstitial volume from the recombinant protein has been removed, wherein substantially not allowing any of the recombinant protein that has been provided to the other of the third interstitial and fourth interstitial volumes to re-enter the interstitial volume from which the recombinant protein has been removed; and (j) maintaining steps (h) and optionally (i) until the desired amount of recombinant protein has been removed from the mixture, wherein the recombinant protein obtained has at least about 70% purity and at least about 70% recovery from the starting mixture.

Preferably, the pH of the solvent or buffer in the first interstitial and second interstitial volumes is greater than the pI of the selected compounds such that the selected compounds are negatively charged.

Preferably, the pH of the solvent or buffer in the third interstitial and fourth interstitial volumes is greater than the pI of the recombinant protein such that the recombinant protein is negatively charged.

More particularly, the method comprises:

(a) placing the mixture in a first sample stream, the first sample stream being separated from a first product stream by a first ion-permeable separation membrane having a molecular mass cut-off less than the molecular mass of the recombinant protein; the first sample and product streams being separated from a first electrophoresis buffer stream by first and second ion-permeable restriction membranes configured to allow the movement of ions and small macromolecules during application of a voltage potential, the first sample and product steams are positioned between a first cathode in a first cathode zone and a first anode in a first anode zone, the first anode disposed relative to the first cathode so as to be adapted to generate an electric field in a first electric field area therebetween upon application of a voltage potential between the first cathode and the first anode;

(b) selecting a buffer or solvent for the first sample stream having a pH such that the recombinant protein or other compounds in the sample have a desired charge;

(c) applying a first voltage potential between the first sample and first product streams causing movement of compounds in the mixture having a molecular mass less than the recombinant protein through the first separation membrane into the first product stream while the recombinant protein is substantially retained in the first sample stream, or if entering the first separation membrane, being substantially prevented from passing through the first separation membrane;

(d) optionally, periodically stopping and reversing the first voltage potential to cause movement of the recombinant protein having entered the first separation membrane to move back into the first sample stream, wherein substantially not causing any compounds that have entered the first product stream to re-enter first sample stream;

(e) maintaining steps (c) and optionally (d) until the desired amount of compounds having a molecular mass less than the recombinant protein have been removed from the mixture in the first sample stream;

(f) placing the mixture obtained in step (e) in a second sample stream, the second sample stream being separated from a second product stream by a second ion-permeable separation membrane having a molecular mass cut-off greater than the molecular mass of the recombinant protein, the second sample and second product streams being separated from a second electrophoresis buffer stream by third and fourth ion-permeable restriction membranes configured to allow the movement of ions and small macromolecules during application of a second voltage potential, the second sample and product streams are positioned between a second cathode in a second cathode compartment and a second anode in a second anode compartment, the second anode disposed relative to the second cathode so as to be adapted to generate an electric field in a second electric field area therebetween upon application of a voltage potential between the second cathode and the second anode;

(g) selecting a buffer or solvent for the first interstitial volume having a pH such that the recombinant protein or other compounds in the sample have a desired charge;

(h) applying a second voltage potential between the second sample and product streams causing movement of the recombinant protein in the mixture through the second separation membrane into the second product stream while other compounds in the mixture are substantially retained in the second sample stream, or if entering the separation membrane, being substantially prevented from passing through the membrane to the second product stream;

(i) optionally, periodically stopping and reversing the second voltage potential to cause movement of the other compounds having entered the second separation membrane to move back into the second sample stream, wherein substantially not causing any recombinant proteins that have entered the second product stream to re-enter the second sample stream; and (j) maintaining steps (h) and optionally (i) until the desired amount of the recombinant protein has been removed from the mixture into the second product stream.

Preferably, the recombinant protein has at least about 70% purity and at least about 70% recovery from the starting mixture.

Preferably, the pH of the solvent or buffer in the first interstitial and second interstitial volumes is greater than the pI of the selected compounds such that the selected compounds are negatively charged.

Preferably, the pH of the solvent or buffer in the third interstitial and fourth interstitial volumes is greater than the pI of the recombinant protein such that the recombinant protein is negatively charged.

Preferably, the second cathode, second cathode buffer zone, second anode, second anode buffer zone, and the second electrophoretic buffer are contiguously disposed in a secondary separation system.

In one embodiment, the mixture is culture media containing the recombinant protein expressed and excreted, obtained or transported extracellularly by a recombinant microorganism. Alternatively, the mixture is a cell lysate of a recombinant microorganism that expresses the protein but does not necessarily excrete or transport the protein extracellularly. If the recombinant protein is secreted from the cells, the culture medium is usually processed first to remove cells. Centrifugation, filtration or flocculation are examples of suitable techniques used to remove cells. After the cells have been removed, the mixture can be diluted or treated prior to being processed by the present invention. For recombinant microorganisms that do not secrete the recombinant protein, the cells are typically lysed or treated so the recombinant protein is released into solution. Lysing is achieved by a number of means including by pressure or osmotic shock. The cell lysate may be centrifuged or filtered to remove cell debris prior to processing by the present invention.

Preferably, the ion-permeable separation membrane is an electrophoresis separation membrane having a molecular mass cut-off from about 40 to about 1000 kDa. The size of the membrane cut-off will depend on the size of the recombinant protein and the other biomolecules in the mixture.

Buffers that have been found to be particularly suitable for the methods according to the present invention are Tris Borate around pH 9 and GABA (Gamma amino butyric acid). It will be appreciated, however, that other buffers are used, depending on the protein to be separated. The concentration of the selected buffers influences or affects the movement of macromolecules through the separation membranes. Typically concentrations of from up to about 200 mM, more preferably from about 20 mM to about 80 mM, have been found to be particularly suitable.

The concentration of the selected buffers also influences or affects the movement of biomolecules and compounds including recombinant proteins through the separation membranes.

In one embodiment, the separated recombinant protein is subsequently concentrated using a system incorporating an electrophoresis separation membrane having a molecular mass cut-off less than the molecular mass of the recombinant protein.

The methods according to the present invention result in yields of greater than about 70% with purity at least about 90%.

The benefits of the methods according to the present invention are the possibility of scale-up without denaturing or adversely altering the physical or biological properties of the recombinant protein.

In an seventh aspect, the present invention provides a recombinant protein purified or separated by the methods according to the present invention.

In a eighth aspect, the present invention relates to use of the recombinant protein according to the eighth aspect of the present invention in medical and veterinary applications.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

Modes for Carrying Out the Invention

Figure 8:
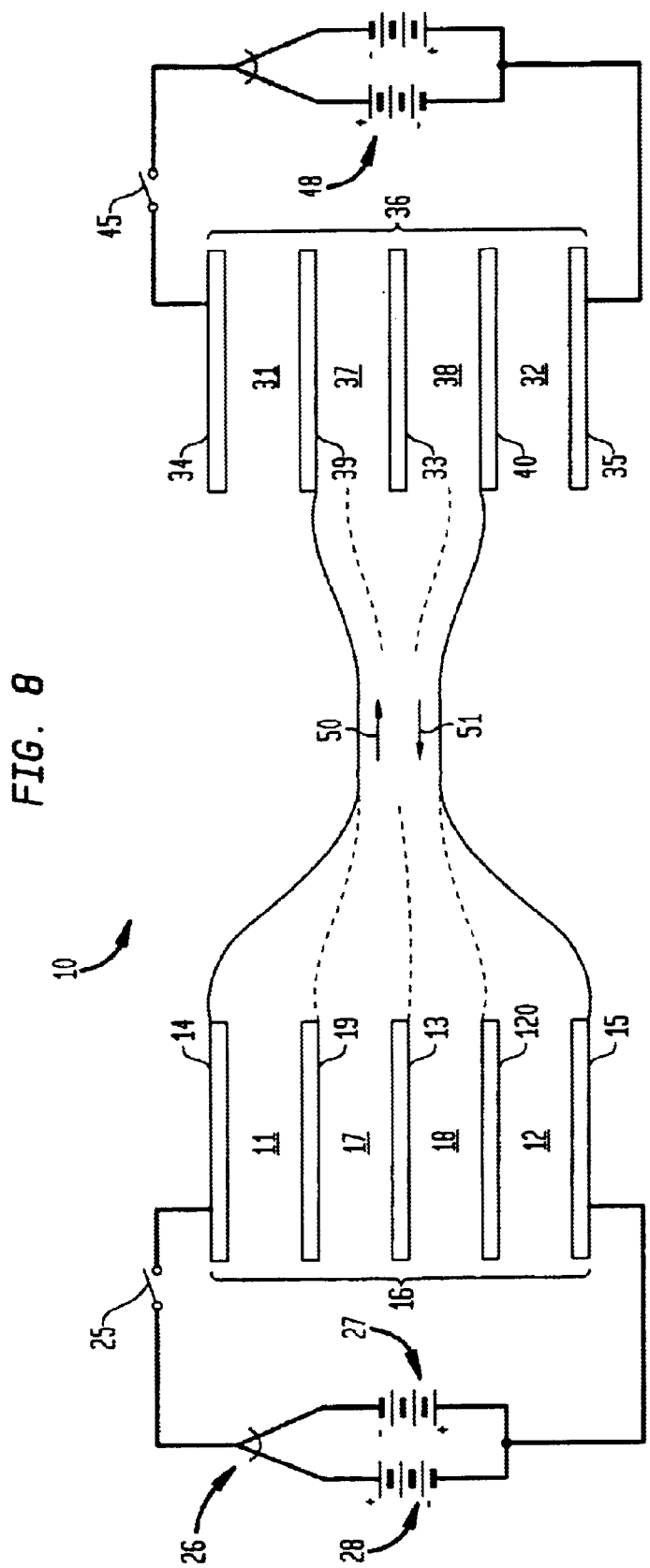
FIG. 8 shows a schematic view of a preferred embodiment of the separation system or apparatus of the present invention.

FIG. 8 shows a preferred embodiment of the apparatus 10 of the present invention. The apparatus 10 includes a first cathode zone or compartment 11 and a first anode zone or compartment 12 separated by membranes 19, 13 and 20. Electrodes 14 and 15 are provided inside the electrode zones or compartments so as to be on opposite sides of the first separation membrane 13 and first and second restriction membranes 19 and 20. It is understood, however, that in another embodiment, the electrodes are positioned outside the buffer compartments. The electrodes are used to apply an electrophoretic potential across the first separation membrane.

A first chamber 17 is positioned between the first cathode compartment 11 and the first separation membrane 13. The first chamber is defined on one side by the first separation membrane 13 and on the other side by a first restriction membrane 19. It is understood, however, that in another embodiment, the first chamber is positioned between the anode buffer compartment and the separation membrane.

A second chamber 18 is positioned between the first anode buffer compartment 12 and the first separation membrane 13. The second chamber is defined on one side by the first separation membrane 13 and on the other side by a second restriction membrane 20 on the other side. It is understood, however, that in another embodiment, the second chamber is positioned between the cathode buffer compartment and the first separation membrane.

The apparatus is further comprised of switch 25 for selection of the application of a first voltage source (such as to turn the voltage source off or have resting periods), switch 26 to switch current direction for cathode/anode or to have reversal periods, and voltage sources 27 and 28.

The apparatus 10 includes a second cathode zone or compartment 31 and a second anode zone or compartment 32 separated by three membranes 39, 33 and 40. Electrodes 34 and 35 are provided inside the electrode zones or compartments so as to be on opposite sides of the separation membrane 33 and restriction membranes 39 and 40. It is understood, however, that in another embodiment, the electrodes are positioned outside the buffer compartments. The electrodes are used to apply an electrophoretic potential across the separation membrane.

A third chamber 37 is positioned between the cathode compartment 31 and the separation membrane 33. The third chamber is defined on one side by the separation membrane 33 and on the other side by a fast restriction membrane 39. It is understood, however, that in another embodiment, the third chamber is positioned between the anode buffer compartment and the separation membrane.

A fourth chamber 38 is positioned between the anode compartment 32 and the second separation barrier 33. The fourth chamber is defined on one side by the second separation membrane 33 and on the other side by a fourth restriction membrane 40 on the other side. It is understood, however, that in another embodiment, the fourth chamber is positioned between the second anode compartment and the second separation membrane.

The apparatus is further comprised of switch 45 for selection of the application of a second voltage source (such as to turn the voltage source off or have resting periods), switch 46 to switch current direction for cathode/anode or to have reversal periods, and voltage sources 47 and 48.

In use, buffer in the first cathode 11 and first cathode 12 compartments or zones is fed by flow 50 to the third chamber or interstitial volume 37 where small compounds in the buffer are caused to move into the fourth chamber 38. The buffer is then recycled by flow 51 back to the first cathode 11 and first cathode 12 compartments or zones.

During purification or processing of samples containing mixtures of compounds, proteins or other macromolecules using an apparatus or system according to the present invention, there is a gradual contamination of electrophoresis buffer with small macromolecules. This "contamination" can be clearly seen in FIGS. 1 and 2.

By cycling buffer from an albumin separation through an apparatus with an open upper restriction membrane and open separation membrane but with a closed lower restriction membrane in a single pass fashion, the majority of small molecular mass proteins can be removed from the buffer. On execution of a second pass it was then possible to remove the final remnants of protein from the solution whilst maintaining pH and conductivity as shown in FIG. 3. Further assessment of this process using OD280, and silver and Sypro ruby (BioRad) protein stains in combination with SDS-PAGE has shown that a large percentage of the contaminants entering the buffer stream during a run are successfully removed.

Figure 4:
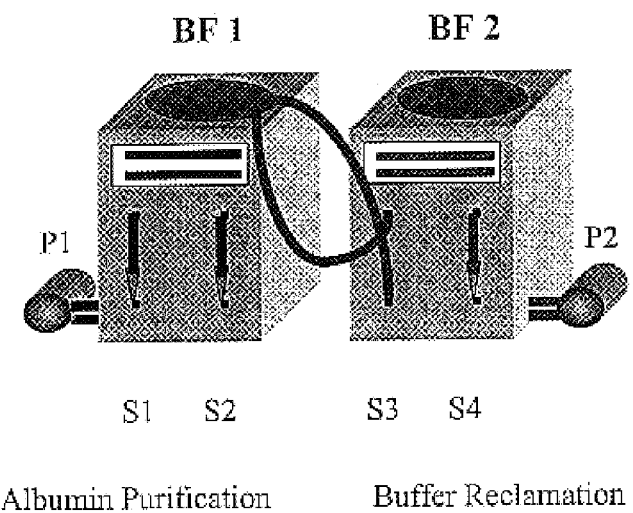
FIG. 4 is a stylised diagram of an online buffer reclamation scheme. A first apparatus according to the present invention (BF1) was used for the protein purification and a second apparatus according to the present invention (BF2) cleaned the buffer stream of BF1 whilst the separation was being carried out.

It has also been shown that a large proportion of the small molecular mass contaminants are removed from buffer whilst the separation is in operation using a second apparatus to process the buffer stream as shown in FIG. 4. This online buffer reclamation has many advantages in that the buffer can be cleaned throughout a run effectively reducing the amount of buffer required to carry out a separation and eliminating the need to change the buffer during a run. The life of the buffer can be increased so that for commercial scale separations the amount of buffer needed can be brought down to a smaller level.

Currently in the research scale machines when using 5 mL of plasma as a starting complex protein mix, 1.5–1.8 liters of buffer are cycled through the buffer stream. For a larger scale machine the amount of buffer needed can be reduced as more efficient cooling systems are used. A sixty times scale up model would require 50 L of buffer. If the starting amount of plasma is increased to 100 liters then an extrapolation of the buffer stream requirements means that 17000 liters of buffer would be required to carry out a separation. This can be an unacceptably large volume of buffer that would incur large overhead costs, such as buffer components, water, and also storage and cooling of these large volumes of buffer. The ability to use a smaller volume of buffer would be of huge commercial advantage in this type of setting.

For a 20× scale up model of the present invention, 250 mL of plasma was processed. Using this volume of plasma per square centimeter of membrane equates to 6700 L of buffer for 100 L of plasma to be separated when using an industrial scale system. Taking into account the cost per liter of buffer for a typical albumin separation using pH 9 Tris-Boric Acid buffer, the cost per run allowing for one buffer change is more than $7,000.

A single apparatus attached to the buffer stream of another apparatus which is carrying out a separation has the ability to remove at least 15% of the contaminants from the buffer stream through out the run. The reduction of 15% in the buffer volume from recycling through just one separation unit would produce a saving of around 3600 L of buffer for a single separation.

In a large-scale unit, it is envisaged that many cartridges could be stacked upon each other in a sandwich arrangement that would enable the introduction of several buffer reclamation streams without any problems. The use of several buffer reclamation streams would reduce the need to change buffer for a single separation and also allows for a much smaller amount of buffer to be used in the buffer stream. If the buffer is recycled and used for two separations, then considerable savings would be made in the separation of one hundred liters of plasma. Considering some companies process hundreds of thousands of liters of plasma per year the savings would be quite substantial.

Recombinant DNA technology has provided a powerful tool for the development of new therapeutic and diagnostic products. A major difficulty in utilising these products however lies in isolating them from culture fluid in high purity and with high recoveries. The present invention provides a novel manner in which recombinant proteins, including recombinant monoclonal antibodies, is isolated from their expression media with minimal loss of product or its activity.

EXAMPLE 1

Recombinant Monoclonal Antibody

Chinese Hamster Ovary (CHO) cell expression media, containing a recombinant monoclonal antibody, was placed in the upstream of an apparatus according to the present invention. The antibody was purified in a two-phase process in which contaminating proteins were removed on the basis of charge and size. Phase 1 involved the use of a Tris Borate buffer at pH 8.0. At this pH, the target antibody stayed in the first interstitial volume whilst contaminating proteins were transferred using 250 V through a 300 kDa pore size separation membrane to the product stream where the contaminants were collected and harvested at regular intervals. The recombinant protein remained in the treated first interstitial volume. Phase 1 was run for 90 minutes.

Phase 2 involved a buffer change to pH 4.2 using GABA (Gamma amino butyric acid 24 mM acetic acid 133 mM) where the target protein (recombinant monoclonal antibody) was positively charged. The antibody was then transferred from the treated first interstitial volume using 250V reversed polarity to the downstream where it was concentrated and harvested at regular intervals. Phase 2 was run for 180 minutes.

Figure 5:
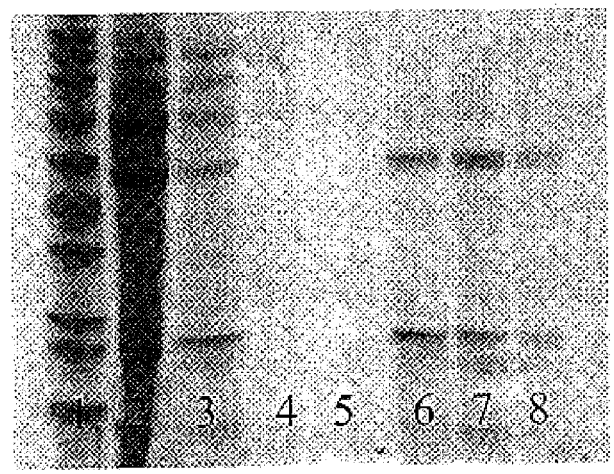
FIG. 5 shows a reduced SDS PAGE gel (8–18% gradient) analysis of a recombinant monoclonal antibody separated according to the present invention.

The target recombinant monoclonal antibody was purified from CHO media in a two-phase process. The product purity was analysed using reduced SDS PAGE as shown in FIG. 5. The characteristic heavy and light chains of immunoglobulin G (IgG) were evident and purity was estimated to be greater than 95%. Minimal contamination was observed using Coomassie stain.

Product recovery was determined using OD 280 nm readings and was calculated to be 87% of the starting material. Starting concentrations were determined using a Behring BN 100 nephelometer in combination with a DADE Behring IgG nephelometer reagent. Assays were performed according to manufacturer's instructions.

A recombinant monoclonal antibody was purified from CHO media in a two-phase isolation process that resulted in 87% recovery of the starting product. The purity was estimated to be greater than 95% based upon SDS PAGE analysis.

EXAMPLE 2

Peridinin-Chlorophyll Protein (PCP)

PCP (peridinin chlorophyll protein) was expressed as a recombinant protein in *Escherichia coli* as inclusion bodies, which were harvested, and solubilised in hot Tris-HCl in preparation for application to a electrophoresis separation apparatus suitable for use in methods according to the present invention.

The recombinant PCP protein was purified in a two phase separation, the first phase simultaneously concentrated the total proteins and changed the buffer environment in which they occurred. The second phase purified the PCP protein on the basis of its size.

In Phase 1, the solubilised PCP inclusion body sample, containing a minimum of 5 mg total protein, was placed into the upstream of an electrophoresis separation apparatus. The buffer utilised for phase 1 consisted of 40 mM HEPES (N-2-Hydroxyethylpiperazine-N'-ethanesulphonic acid) and 28 mM Tris at pH 7.5. At this pH of 7.5, the PCP and other proteins in the solubilised inclusion body sample transferred through a 1000 kDa pore size separation membrane into a smaller volume product stream at a constant current of 500 mA. The product stream was harvested at the completion of the Phase 1 separation at 90 minutes. The product stream contained the majority of the proteins present in the inclusion body sample in a smaller volume, and in the HEPES/ Tris buffer at pH 7.5.

The harvested product stream of Phase 1 was placed into the upstream of an electrophoresis separation apparatus. Phase 2 involved the separation of PCP from the contaminating proteins using a size-based strategy. The PCP protein has a size of 32 kDa. The buffer utilised for Phase 2 was identical to the buffer utilised in Phase 1 which was a 40 mM HEPES and 28 mM Tris pH 7.5. The PCP protein transferred through a 50 kDa pore size separation membrane and was retained in the product stream. Contaminating proteins of larger molecular weight did not transfer through the 50 kDa pore size separation membrane and were retained in upstream. Contaminating proteins smaller than PCP transferred through the 50 kDa pore size separation membrane and also through a 20 kDa pore size lower (anode/positive electrode) restriction membrane into the recirculating buffer stream. The pore size of the upper (cathode/negative electrode) restriction membrane was 5 kDa to prevent the smaller contaminating proteins from re-entering the upstream and product streams. The PCP protein was harvested from the product stream at the conclusion of Phase 2 at 120 minutes.

Figure 6:
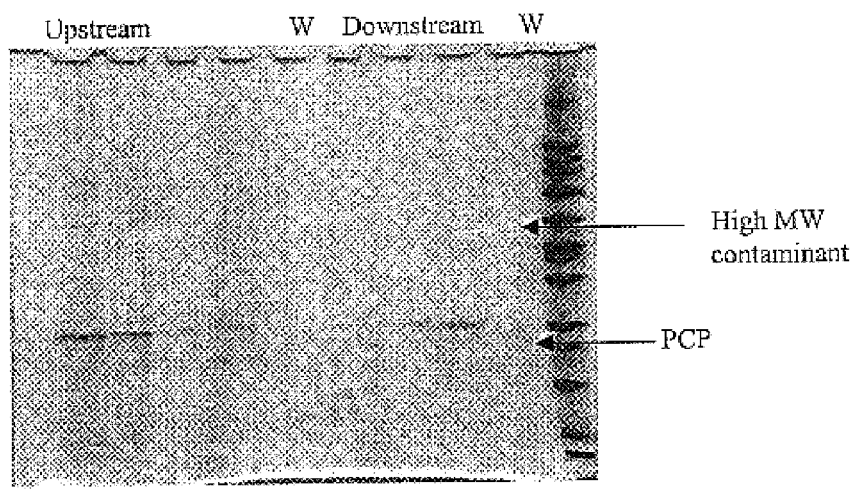
FIG. 6 shows Coomassie stained non-reduced SDS-PAGE of 50 kDa separation. Samples were taken at 0, 60, 90, 120 mins upstream and 60, 90, 120 mins downstream prior to analysis. W denotes a PBS wash.
Figure 7:
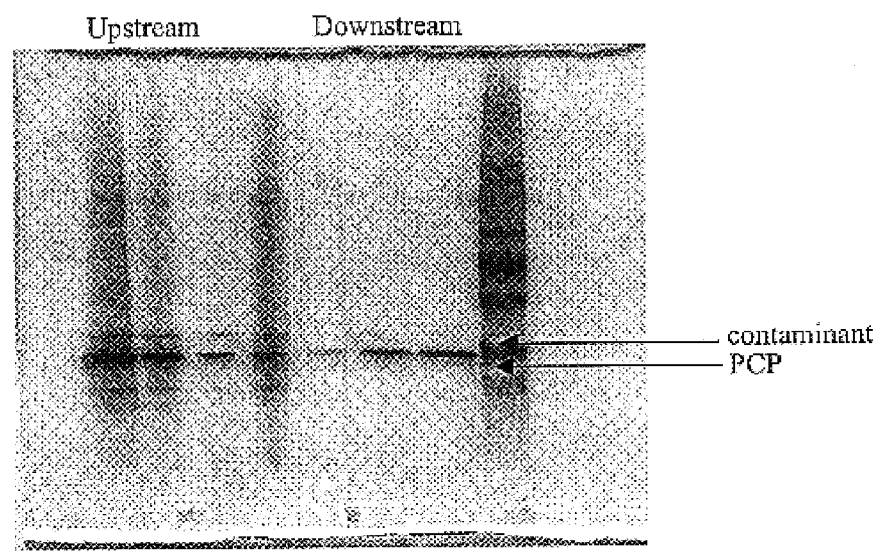
FIG. 7 shows silver stain of 50 kDa separation. Samples are as for FIG. 4 but omitting the wash fraction (W). The higher molecular mass contaminant that showed up on the Coomassie stained gel did not show up on the silver stain (negatively stained).

PCP was separated from a solubilised *E. coli* inclusion body sample using a two phase process. Purity of the harvested PCP was determined using Coomassie and silver staining of non-reduced SDS-PAGE (FIGS. 6 and 7). Purity of the PCP was assessed as being greater than 90%.

Protein recovery was assessed using bicinchoninic acid protein assays. For an initial total protein of 6.8 mg in the *E. coli* inclusion body sample, the PCP sample harvested from the product stream of Phase 2 contained 1.8 mg of protein. This was estimated by Coomassie and silver staining of non-reduced SDS-PAGE to be at least 80% of the PCP in the original sample.

Recombinant PCP, expressed in *E. coli* as inclusion bodies, was purified using a two phase strategy. The PCP protein recovered was estimated to be greater than 80% of the PCP protein present in the starting material. The purity of the final PCP sample was estimated to be greater than 90%.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What we claim is:

1. A system for separating macromolecules by electrophoretic separation, comprising:

(a) a first cathode in a first cathode zone;

(b) a first anode in a first anode zone;

(c) a first restriction barrier disposed between the first cathode zone and a first separation barrier so as to define a first interstitial volume therebetween;

(d) a second restriction barrier disposed between the first anode zone and the first separation barrier so as to define a second interstitial volume therebetween;

(e) pumping means to transport a selected separation product contained in the sample constituent from a selected one of the first interstitial and second interstitial volumes to the other of the first and second interstitial volumes upon application of a first voltage potential, wherein the selected separation product is removed from the sample constituent through the first separation barrier and transported to the other of the first and second interstitial volumes;

(e) a third restriction barrier disposed between a second cathode zone and a second separation barrier so as to define a third interstitial volume therebetween;

(f) a fourth restriction barrier disposed between a second anode zone and the second separation barrier so as to define a fourth interstitial volume therebetween; and (g) pumping means to recirculate a first electrophoretic buffer from a selected one of the third and fourth interstitial volumes back to a selected one of the first interstitial volume, the first cathode zone and the first anode zone after the selected separation product has been removed from the first electrophoretic buffer.

2. The system according to claim 1, wherein the second cathode zone, second anode zone, and a second electrophoretic buffer are contiguously disposed in a secondary separation system.

3. The system according to claim 1 wherein the separation barriers are membranes comprised of polyacrylamide and have a molecular mass cut-off from about 1 to about 1500 kDa.

4. The system according to claim 1 wherein the first and second restriction barriers are membranes comprised of polyacrylamide and have a molecular mass cut-off less than the first separation membrane.

5. The system according to claim 4 wherein the restriction membranes have a molecular mass cut-off from about 1 kDa to about 100 kDa.

6. The system according to claim 5 wherein the restriction membranes have a molecular mass cut-off of about 5 kDa.

7. The system according to claim 1 wherein the first and second interstitial volumes are provided as a cartridge positioned between the first cathode zone and the first anode zone forming first upstream and downstream interstitial volumes.

8. The system according to claim 1 wherein the third and fourth interstitial volumes are provided as a cartridge positioned between the second cathode zone and the second anode zone forming second upstream and downstream interstitial volumes.

9. A method for removing small macromolecule contaminants from a sample constituent, comprising:

(a) placing a sample constituent into a selected one of the first interstitial volume and second interstitial volume of an electrophoretic apparatus according to claim 1;

(b) applying a first voltage potential between the first and second interstitial volumes wherein upon application of the first voltage potential, a selected separation product is removed from the sample constituent through the first separation barrier and provided to the other of the first and second interstitial volumes;

(c) passing a first electrophoretic buffer containing the small macromolecules to a selected one of the third and fourth interstitial volumes;

(d) allowing movement of small macromolecule contaminants through the second separation barrier to the other of the third and fourth interstitial volumes while substantially preventing the first electrophoretic buffer from passing to the other of the third and fourth interstitial volumes;

(e) optionally applying a second voltage potential between the third and fourth interstitial volumes to assist step (d); and (f) returning the first electrophoretic buffer after the selected separation product has been removed, to a selected one of the first cathode zone and first anode zone.

10. The method according to claim 9, further comprising periodically stopping and reversing the first voltage potential between the first and second interstitial volumes to move any desired macromolecules other than the small macromolecule contaminants back into a selected one of the first and second interstitial volumes in which the sample constituent was placed while substantially preventing small macromolecule contaminants that have entered the other of the first and second interstitial volumes from returning to the selected one of the first and second interstitial volumes.

11. The method according to claim 9, further comprising separating desired macromolecules in the sample constituent by size and charge across the first separation barrier into the other of the first and second interstitial volumes.

12. The method according to claim 9 whereby the small macromolecule contaminants move through at least the first separation barrier or the first restriction barriers in step (b).

13. The method according to claim 9 further comprising applying a first or second electric potential of about 250 V and current of about 500 mA.

14. The system according to claim 1, wherein the sample constituent is selected from the group consisting of blood-derived products including plasma, antibody samples, samples containing biomolecules including proteins, peptides, glycoproteins, oligonucleotides, recombinant proteins, cell extracts, cell culture supernatant, growth factors, antigens, immunogens, and combinations thereof.

15. The system according to claim 1, wherein the second separation barrier is disposed between the third and fourth interstitial volumes such that small macromolecule contaminants move through the second separation barrier into a selected one of the third and fourth interstitial volumes while substantially preventing the first electrophoretic buffer from passing to such interstitial volume.

16. The system according to claim 15, wherein the small macromolecule contaminants are selected from the group consisting of peptides, protein fragments, other small molecular mass contaminants, and combinations thereof.

17. The system according to claim 16 wherein the small macromolecule contaminants have a molecular mass of from about 500 Da to about 100 kDa.

* * * * *